United States Patent
Hoyos Ariza

(10) Patent No.: US 10,980,925 B1
(45) Date of Patent: *Apr. 20, 2021

(54) HIGH DEFINITION LIPOSCULPTURE

(71) Applicant: A Hoyos LLC, Miami, FL (US)

(72) Inventor: Alfredo Ernesto Hoyos Ariza, Miami, FL (US)

(73) Assignee: A HOYOS LLC, Miami, FL (US)

( * ) Notice: Subject to any disclaimer, the term of this patent is extended or adjusted under 35 U.S.C. 154(b) by 369 days.

This patent is subject to a terminal disclaimer.

(21) Appl. No.: 15/895,150

(22) Filed: Feb. 13, 2018

Related U.S. Application Data

(63) Continuation-in-part of application No. 14/532,452, filed on Nov. 4, 2014, now Pat. No. 9,888,933, which is a continuation-in-part of application No. 13/461,027, filed on May 1, 2012, now Pat. No. 8,876,799, which is a continuation-in-part of
(Continued)

(51) Int. Cl.
*A61M 1/00* (2006.01)
*A61B 17/32* (2006.01)
*A61B 17/00* (2006.01)
*A61B 90/00* (2016.01)

(52) U.S. Cl.
CPC ... *A61M 1/0084* (2013.01); *A61B 17/320068* (2013.01); *A61B 2017/00792* (2013.01); *A61B 2017/32007* (2017.08); *A61B 2090/3908* (2016.02); *A61M 2202/08* (2013.01)

(58) Field of Classification Search
CPC .......... A61B 2018/00464; A61B 2017/00792; A61M 2202/08
See application file for complete search history.

(56) References Cited

U.S. PATENT DOCUMENTS 1,761,278 A 1/1930 Redmond
1,859,198 A 5/1932 Cunningham
(Continued)

FOREIGN PATENT DOCUMENTS

WO WO 9944514 9/1999
WO WO 0041671 A2 7/2000

OTHER PUBLICATIONS

De Souza Pinto et al., Superficial liposuction of the back and waist, Operative Techniques in Plastic and Reconstructive Surgery, vol. 3 No. 2 (May), 1996: pp. 106-116.*
(Continued)

*Primary Examiner* — Susan S Su
(74) *Attorney, Agent, or Firm* — Malloy & Malloy, P.L.

(57) ABSTRACT

A surgical procedure for performing liposculpture on the human body comprising defining a surgical site where the liposculpture is to be performed including substantially 360 about at least the torso portion of the body and/or the limbs. The surgical site is infiltrated with a predetermined quantity of solution and subsequently performing multi-layer emulsification of fat deposits about the surgical site utilizing an ultrasound technology, wherein the multi-layer emulsification includes at least a superficial layer emulsification of fat deposits and a deep layer emulsification of fat deposits. Subsequently, a multi-layer liposuction extraction of the emulsified fat deposits is performed, wherein the multi-layer liposuction extraction comprises a deep layer liposuction; a superficial layer liposuction and an intermediate layer liposuction.

12 Claims, 1 Drawing Sheet

Related U.S. Application Data application No. 12/287,816, filed on Oct. 14, 2008, now Pat. No. 8,167,868.

(56) References Cited

U.S. PATENT DOCUMENTS

| | | |
|---|---|---|
| 2,105,605 A | 1/1938 | Lichtenstein |
| 2,492,489 A | 12/1949 | Levinthal |
| 2,505,720 A | 4/1950 | Peiser et al. |
| 2,697,224 A | 12/1954 | Aidenland |
| 3,598,114 A | 8/1971 | Lewis |
| 3,956,784 A | 5/1976 | Vargas |
| 4,508,110 A | 4/1985 | Modglin |
| 4,519,385 A | 5/1985 | Atkinson et al. |
| 4,676,780 A | 6/1987 | Lee |
| 4,679,261 A | 7/1987 | Stanley et al. |
| 4,722,332 A | 2/1988 | Saggers |
| 4,824,062 A | 4/1989 | Wagner |
| 4,941,872 A | 7/1990 | Felix et al. |
| 4,960,161 A | 10/1990 | Easley |
| 4,982,739 A | 1/1991 | Hemstreet et al. |
| 5,067,542 A | 11/1991 | Easley |
| 5,102,127 A | 4/1992 | Pohrer |
| 5,147,292 A | 9/1992 | Kullas et al. |
| 5,158,531 A | 10/1992 | Zamosky |
| 5,181,907 A | 1/1993 | Becker |
| 5,186,714 A | 2/1993 | Boudreault et al. |
| 5,230,704 A | 7/1993 | Moberg et al. |
| 5,255,669 A | 10/1993 | Kubota et al. |
| 5,285,909 A | 2/1994 | Slater |
| 5,318,012 A | 6/1994 | Wilk |
| 5,329,943 A | 7/1994 | Johnson |
| 5,398,671 A | 3/1995 | Ortiz et al. |
| 5,419,761 A | 5/1995 | Narayanan et al. |
| 5,460,169 A | 10/1995 | Mouret |
| 5,501,653 A | 3/1996 | Chin |
| D373,944 S | 9/1996 | Thompson et al. |
| 5,569,165 A | 10/1996 | Chin |
| 5,643,198 A | 7/1997 | Cucin |
| 5,658,328 A | 8/1997 | Johnson |
| 5,660,422 A | 8/1997 | Knisley |
| 5,683,366 A | 11/1997 | Eggers et al. |
| 5,718,670 A | 2/1998 | Bremer |
| 5,823,984 A | 10/1998 | Silverberg |
| 5,884,631 A | 3/1999 | Silberg |
| 5,935,143 A | 8/1999 | Hood |
| 5,996,791 A | 12/1999 | Bibby et al. |
| 6,071,260 A | 6/2000 | Halverson |
| 6,241,747 B1 | 6/2001 | Ruff |
| 6,253,907 B1 | 7/2001 | Lachmann et al. |
| 6,276,175 B1 | 8/2001 | Broder, Jr. |
| 6,315,745 B1 | 11/2001 | Kloecker |
| 6,368,299 B1 | 4/2002 | Cimino |
| 6,436,064 B1 | 8/2002 | Kloecker |
| 6,450,975 B1 | 9/2002 | Brennan et al. |
| 6,461,350 B1 | 10/2002 | Underwood et al. |
| 6,524,250 B1 | 2/2003 | Weber et al. |
| 6,585,673 B1 | 7/2003 | Bass |
| 6,629,942 B1 | 10/2003 | Tubbs |
| 6,852,089 B2 | 2/2005 | Kloecker et al. |
| 6,878,142 B2 | 4/2005 | Lawrence et al. |
| 6,920,883 B2 | 7/2005 | Bessette et al. |
| 7,331,951 B2 | 2/2008 | Eshel et al. |
| 7,857,773 B2 | 12/2010 | Desilets et al. |
| 7,909,802 B2 | 3/2011 | Sauter et al. |
| D650,480 S | 12/2011 | Scholly |
| 8,105,256 B1 | 1/2012 | Ariza |
| 8,114,117 B2 | 2/2012 | Avitable |
| 8,167,868 B1 | 5/2012 | Ariza |
| 8,425,490 B2 | 4/2013 | Ariza |
| 8,430,830 B1 | 4/2013 | Ariza |
| 8,506,476 B1 | 8/2013 | O'Mara, Jr. |
| 8,506,509 B1 | 8/2013 | Ariza |
| D696,781 S | 12/2013 | Norton |
| 8,876,799 B1 | 11/2014 | Ariza |
| D719,651 S | 12/2014 | Hoffmann et al. |
| D739,017 S | 9/2015 | Renner |
| D746,460 S | 12/2015 | Gitman |
| 9,248,228 B2 | 2/2016 | Bono et al. |
| D773,915 S | 12/2016 | Barakat et al. |
| D802,769 S | 11/2017 | Robertson et al. |
| D809,893 S | 2/2018 | Hsien-Te |
| D811,605 S | 2/2018 | Chang |
| 9,888,933 B1 | 2/2018 | Hoyos Ariza |
| 9,907,602 B2 | 3/2018 | Fedenia et al. |
| D824,130 S | 7/2018 | Vosbikian et al. |
| D824,626 S | 7/2018 | Vosbikian et al. |
| D825,765 S | 8/2018 | Yang et al. |
| D858,763 S | 9/2019 | Zimmerli et al. |
| D860,756 S | 9/2019 | Lindo |
| 2002/0106970 A1 | 8/2002 | Falla |
| 2003/0032961 A1 | 2/2003 | Pelo et al. |
| 2004/0162546 A1 | 8/2004 | Liang |
| 2004/0186353 A1 | 9/2004 | Palermo |
| 2004/0206714 A1 | 10/2004 | Jablow |
| 2006/0206714 A1 | 9/2006 | Gubo |
| 2007/0055179 A1 | 3/2007 | Deem |
| 2007/0060989 A1 | 3/2007 | Deem et al. |
| 2008/0078800 A1 | 4/2008 | Hess et al. |
| 2008/0194999 A1 | 8/2008 | Yamaha et al. |
| 2008/0195036 A1 | 8/2008 | Merchant et al. |
| 2009/0248004 A1 | 10/2009 | Altshuler et al. |
| 2010/0057056 A1 | 3/2010 | Gurtner et al. |
| 2010/0130903 A1 | 5/2010 | Rock |
| 2010/0137256 A1 | 6/2010 | Haddad |
| 2010/0155349 A1 | 6/2010 | Murphy |
| 2011/0040287 A1 | 2/2011 | Ference et al. |
| 2011/0144729 A1 | 6/2011 | Weber |
| 2012/0265072 A1 | 10/2012 | Matlock |
| 2013/0066155 A1 | 3/2013 | Keating et al. |
| 2013/0096596 A1 | 4/2013 | Schafer |
| 2014/0088370 A1 | 3/2014 | Giulianotti et al. |
| 2014/0121694 A1 | 5/2014 | Lambert et al. |
| 2017/0273727 A1 | 9/2017 | Roman et al. |
| 2019/0380728 A1 | 12/2019 | Hoyos Ariza |

OTHER PUBLICATIONS

Mladick, R., Intermediate Liposuction, Aesthetic Surgery Quarterly, spring 1996.*

Gasparotti, M., Superficial Liposuction Yields Superior Results for Most Patients, Aesthetic Surgery Journal, Jan./Feb. 1997.* www.9-hfx.com, Unknown Author, accessed Mar. 19, 2013, available as of at least Feb. 1, 2011, as confirmed by http://web.archive.org/web/20110201194313/http://9-hfx.com/.

Hoyos et al., VASER-Assisted High-Definition Liposculpture, Aesthetic Surgery Journal, 2007, 27:594-604 (Nov./Dec. 2007).

Gasperoni et al., Rationale of Subdermal Superficial Liposuction Related to the Anatomy of Subcutaneous Fat and the Superficial Fascial System "Aesthetic Plastic Surgery," 19:13-20 (1995).

Avelar, Regional Distribution and Behavior of the Subcutaneous Tissue Concerning Selection and Indication for Liposuction, "Aesthetic Plastic Surgery," 13:155-165 (1989).

Fischer, Chapter 22: Liposuction of the Trunk, Liposuction Principles and Practice, Springer-Verlag Berling Heidelberg, 2006.

Pitanguy et al., Chapter 23: Liposuction and Dermolipectomy, Liposuction Principles and Practice, Springer-Verlag Berling Heidelberg, 2006.

De la Torr et al., Chapter 24: The Modern Lipoabdominosplasty, Liposuction Principles and Practice, Springer-Verlag Berling Heidelberg, 2006.

Raskin, Chapter 25: Abdominal Liposuction in Colostomy Patients, Liposuction Principles and Practice, Springer-Verlag Berling Heidelberg, 2006.

Raskin, Chapter 27: Microcannula Liposuction, Liposuction Principles and Practice, Springer-Verlag Berling Heidelberg, 2006.

Gasparotti, Chapter 29, Three-Dimensional Superficial Liposculpture for Aged and Relaxed Skin, Liposuction Principles and Practice, Springer-Verlag Berling Heidelberg, 2006.

Cimino, Chapter 34: VASER-Assisted Lipoplasty: Technology and Technique, Liposuction Principles and Practice, Springer-Verlag Berling Heidelberg, 2006.

(56) References Cited

OTHER PUBLICATIONS

Giuseppe, Alberto, Chapter 35: Ultrasound-assisted lipoplasty for face contouring with VASER, Liposuction Principles and Practice, Springer-Verlag Berling Heidelberg, 2006.
Cimino, William, Chapter 32: Ultrasound-assited lipsuction: past, present, and future, Liposuction Principles ad Practice, Springer-Verlag Berling Heidelberg,2006.
Gamage, "Patient-specific modeling of breast biomechanics with applications to breast cancer detection and treatment," in Patient-Specific Modeling in Tomorrow's Medicine, Springer Berlin Heidelberg, p. 379-412, 2011.
Canfield, "Scult My Dream," commercial software website, Canfield Inc., via WayBackMachine at https://web.archive.org/web/20110930111308/http://www.sculptmydream.com/, 2012.
Frank, Paul Jarrod, Advances in Fat-emulsifying Technologies, European Dermatology, vol. 3, 2008.

\* cited by examiner

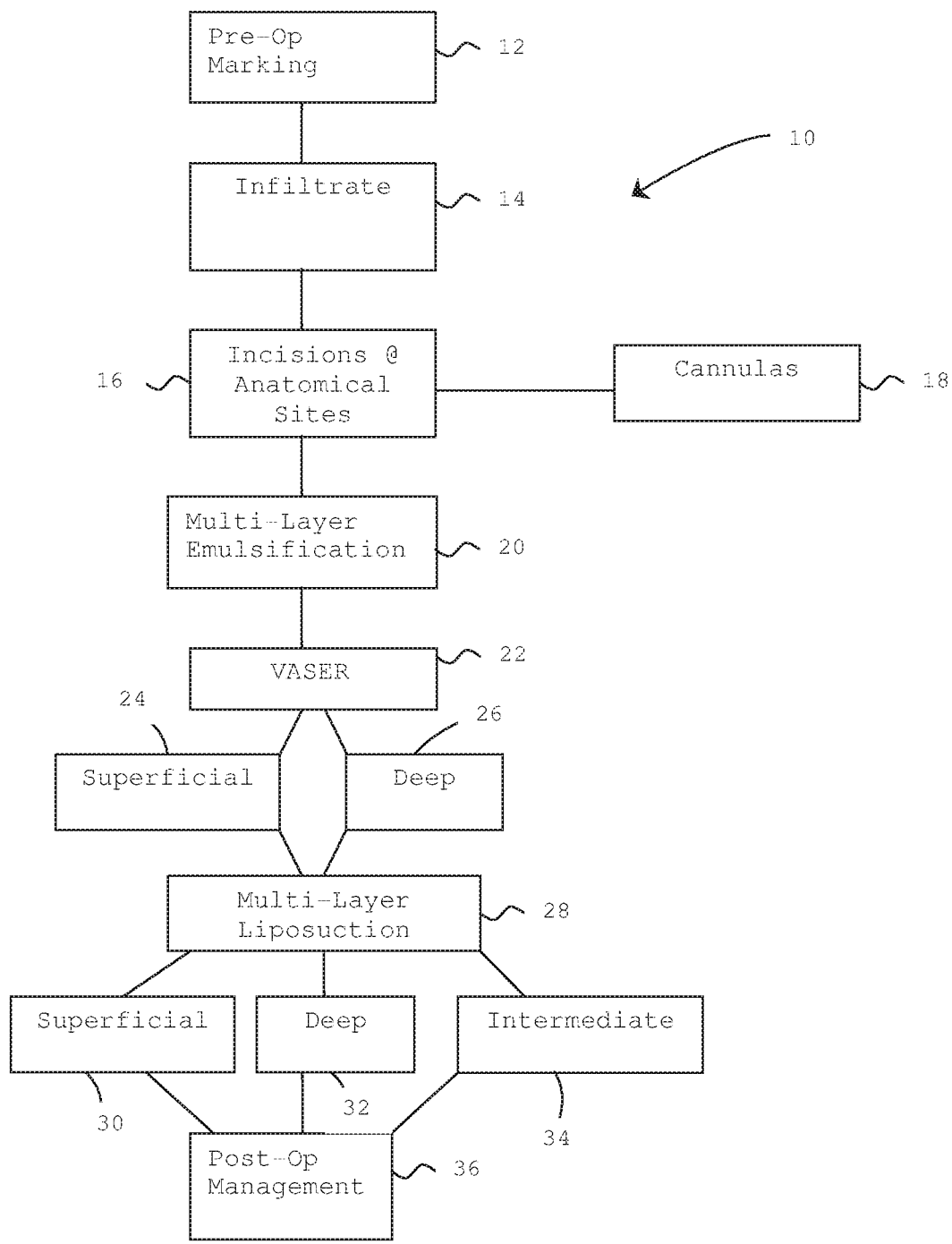

HIGH DEFINITION LIPOSCULPTURE

CLAIM OF PRIORITY

The present application is a Continuation-In-Part application of previously filed patent application having Ser. No. 14/532,452 which was filed on Nov. 4, 2014, which is set to mature into U.S. Pat. No. 9,888,933 on Feb. 13, 2018, which is a continuation-in-part application of previously filed application having Ser. No. 13/461,027, filed on May 1, 2012, which matured into U.S. Pat. No. 8,876,799 on Nov. 4, 2014, which is a continuation-in-part application of previously filed application having Ser. No. 12/287,816, filed on Oct. 14, 2008, which matured into U.S. Pat. No. 8,167,868 on May 1, 2012, which are incorporated herein by reference in their entireties.

BACKGROUND OF THE INVENTION

Field of the Invention

The present invention is directed to a surgical procedure for accomplishing liposculpturing of the human body which incorporates the use of an ultrasound technology. Inclusive in the surgical procedure is the multi-layer emulsification of fat deposits about a surgical site associated with a portion of the body, including at least the torso of the body and/or one or more selected limbs of the body, wherein the surgical site may extend substantially 360° about the selected body portion. Multi-layer liposuction is utilized to extract the emulsified fat deposits resulting in a three-dimensional technique which enhances the natural muscularity of the patient's body.

Description of the Related Art

Lipoplasty is currently the plastic surgical procedure performed most often in the United States, wherein the fundamental technique and technology associated therewith have changed only slightly during the past 30 years. Superficial lipoplasty with standard lipoplasty cannulas expand the boundaries of body contouring by enabling the removal of fat from superficial layers. However, this advance in lipoplasty technique has also involved increased risk of scarring and contour irregularities.

Existing publications indicate that traditional lipoplasty techniques often fail to achieve the aesthetic goal of a "wash board" abdominal contour because sub-dermal fat often obscures the muscular detail. Known techniques referred to as "abdominal etching" use different lipoplasty to detail abdominal musculature, specifically the rectus abdominis muscle, between the linea alba and the linea semilunaris, while also addressing the tendinous inscriptions of the rectus abdominis muscle. However, abdominal etching was designed specifically for the male body having between 8% and 15% body fat and was limited to only interior abdominal wall. Accordingly, female and/or moderately obese patients were not susceptible subjects for the known abdominal etching surgical procedure.

Therefore, there is a need in the area of body sculpturing for a high definition liposculpture surgical procedure which would represent a significant improvement in body contouring. As such, the terms "liposculpture" is utilized to define a surgical technique which does not simply remove fat, but represents an "artistic approach" designed to emulate surface anatomy. Accordingly, a proposed improvement in this area would include "high definition liposculpture" (HDL), which represents a development through the study of art and anatomy of the human musculature as an artistic treatment of the human form to create not only a slim figure but also the appearance of a highly developed musculature. Further, a proposed HDL procedure elevates the concept of abdominal etching to a three-dimensional approach taking into account the contributions made by other muscle groups to integrate the entire or substantially 360 degrees of the torso and in certain instances the limbs, including the legs or arms, as well as back of the body on which the surgical procedure is being performed. As a result, the differing aesthetic goals of male and female body contouring can be integrated into such a proposed procedure which further includes key areas such as pectorals in men and the gluteal area in women.

Further, the proposed unique and improved surgical procedure for body sculpturing may appropriately incorporate the use of ultrasound technology, such as but not limited to "VASER" technology or "Vibration Amplification of Sound Energy at Resonance" with the HDL procedure. This association represents a marriage between technology and technique that allows a more precise, less traumatic procedure with improved outcomes. Accordingly, ultrasound assisted HDL or "UAHDL" allows fat tissue to be prepared for more effective sculpturing through emulsification. As such, the surgeon can "sculpt" muscular anatomy in great detail through gentle extraction aspiration that minimizes the trauma normally associated with traditional lipoplasty. Further, UAHDL embodies the ultimate understanding of how superficial anatomy influences external appearance. As such, UAHDL has been developed through the study of "surface anatomy" of the human musculature much as an artist would view the human form and begins where superficial lipoplasty ends. In addition, the unique surgical procedure defined by UAHDL highlights the importance of contributions made to the aesthetics of the human form by both superficial and deep fat layers when these layers are properly proportioned both between and over the associated muscle groups.

SUMMARY OF THE INVENTION

The present invention is directed to a three-dimensional technique which enhances natural muscularity of the patient and includes transitioning, comprising an intermediate layer liposuction technique to facilitate the enhancement of intended results. As such, high definition liposculpture is utilized in combination with an ultrasound technology to define the present invention comprising "ultrasound assisted high definition liposculpture" or "UAHDL".

The UAHDL procedure of the present invention preliminarily involves a preoperative surgical marking of a patient when in the operating room with the patient initially disposed in a supine position and completed with a patient in an upright standing position. As such, an understanding of superficial anatomy and human typography is important, thereby requiring the surgeon to learn how to examine the patient for individual characteristics in order to avoid inaccurate marking which could possibly lead to deformities and abnormal appearance. In the application of the UAHDL procedure, it is to be noted that the surface anatomy varies between men and women. In women, the transversal lines in the rectus abdominis muscle are not aesthetically desirable because they tend to look too "masculine". In men, the landmarks marked may preferably include pectorals major, serratus interior, rectus abdominis, external oblique, iliac crest and inguinal ligaments as well as the relationship between these structures.

Further, the UAHDL surgical procedure of the present invention comprises both a superficial and deep infiltration performed using solution of 1,000 cc of normal saline as well as 1 cc of epinephrine. Detailed infiltration may be performed in areas that require more superficial works, such as the waist and perigluteal area in women and other areas in the male body. Further, in anticipation of the use of an ultrasound technology, the exact amounts of infiltration in each area and the estimated time of ultrasound use are determined and maintained.

The ultrasound technology is a primary technique for accomplishing emulsification of predetermined fat deposits. Further, the emulsification technique using ultrasound technology is performed preferably in a continuous mode for the high de-bulking and in a pulsed mode at lower power for more delicate areas and the immediate sub-dermal plane. Preferably, the de-bulking was performed using ventilated cannulas, beginning in the deep layers and continuing to the mid-lamellar layer and between muscle groups. Superficial emulsification was performed to define the relevant anatomy of the muscle groups in each treatment area. Transitioning was then performed to define the superficial anatomy landmarks. As used herein "transitioning" comprises the de-bulking or extracting of some of the remaining fat deposits existing over the associated muscle groupings and smoothing the surfaces over the associated anatomical areas, such as the mid-lamellar area.

Accordingly, the UAHDL surgical procedure of the present invention comprises a multi-layer emulsification technique comprising both deep layer emulsification of fat deposits and superficial layer emulsification of fat deposits using ultrasound technology, as described in greater detail herein. Subsequently, multi-layer liposuction is applied to accomplish a more specific definition of the relative anatomy of the muscle groups in each anatomical section of the surgical site, as well as the transitioning of anatomy landmarks by removing the remaining fat over predetermined muscle groups specifically, but not exclusively, in the mid-lamellar area.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a schematic representation in block diagram form representing related and cooperative surgical steps and techniques which collectively define the "ultrasound assisted high definition liposculpture" or "UAHDL" surgical procedure of the present invention.

Like reference numerals refer to like parts throughout the several views of the drawings.

DETAILED DESCRIPTION OF THE PREFERRED EMBODIMENT

The present invention is directed to preferably ultrasound assisted, high definition liposculpture surgical procedure and is a three-dimensional technique which enhances the natural muscularity of the patient resulting in the creation not only of a slim figure for the human body but also the appearance of highly developed muscularity. As such, the ultrasound assisted high definition liposculpture or "UAHDL" is applicable for use on both men and women with less limitations relating to body physique, age, gender, etc. than known or conventional body sculpturing techniques. Distinguishing features of the UAHDL procedure include the use of underlying anatomical structures as a guide to accomplishing the intended three-dimensional body contour.

Further, while the surgical site, in at least one embodiment of the present invention represents 360 degrees about at least the torso portion of the human body, this three-dimensional approach can also take into account the contributions made by other muscle groups to integrate and further define the surgical site to include substantially the entire torso, back and limbs including the legs and arms. The subject UAHDL surgical procedure in the various preferred embodiments of the present invention utilizes the assistance of "vibration amplification of sound energy at resonance" or "VASER" technology as the ultrasound technology. In utilizing ultrasound technology, the UAHDL surgical procedure enables the application of lipoplasty techniques to the superficial fat layers or deposits and overcomes certain disadvantages associated with "abdominal etching" which has limited applicability in terms of gender and obesity of qualified patients.

More specifically, ultrasound technology as applied to the subject UAHDL surgical procedure is preferably performed utilizing a solid probe that generates ultrasound on various multi-layers for purposes of emulsifying fat deposits. As set forth in greater detail, ultrasound technology is used in the performance of multi-layer emulsification of fat deposits at and substantially about 360° of the surgical site. Subsequently multi-layer liposuction was applied to the various anatomical sections to extract the emulsified fat deposits thereby accomplishing the desired sculpturing and muscularity of the patient about the 360° surgical site.

With primary reference to the schematic representation of the accompanying Figure, the UAHDL surgical procedure is generally indicated as 10 and initially comprises preoperative marking 12 of the patient. At least partially dependent on the selected surgical site, the preoperative marking 12 is preferably performed with the patient initially supine and completed with the patient in an upright standing position. Subsequent to the preoperative marking 12, an infiltration of the body about the surgical site, which may include substantially 360° about the surgical site, is accomplished, as at 14. More specifically, the infiltration technique or process 14 comprises the infiltration of a predetermined quantity of saline solution, such as substantially 1,000 cc, and epinephrine, in a predetermined quantity, such as generally 1 cc. This solution is infiltrated about the surgical site, which may include substantially 360° about the surgical site, by performing a plurality of anatomical incisions 16 through which the fluid is introduced using infiltration cannulas 18.

Subsequent to the infiltration procedure, the additional, non-mobile step in the UAHDL surgical procedure involves emulsification, as at 20, and more specifically multi-layer emulsification at the surgical site, which may include substantially 360° about the surgical site. As set forth above, the emulsification of fat deposits is performed using ultrasound technology as at 22 and is preferably performed by a solid probe that generates ultrasound on superficial tissue layers and deep tissue layers. In a preferred embodiment emulsification may first be performed on superficial tissue layers and subsequently on the intermediate or deep tissue layers. The ultrasound probe generates a specific frequency that is selective to fat and accomplishes the emulsification of fat deposits in its path or as applied. Accordingly, with reference to the accompanying Figure, the emulsification 20, utilizing the ultrasound assisted technology 22 involves a multi-layer emulsification comprising at least a superficial layer emulsification of fat deposits, as at 24 and a deep layer emulsification of fat deposits, as at 26. The utilizing the ultrasound assisted technology 22 the multi-layer emulsification may also comprise a superficial layer emulsification of fat deposits, a deep layer emulsification of fat deposits, and an intermediate layer emulsification of fat deposits.

Thereafter, a multi-layer liposuction is performed for the extraction of the emulsified fat deposits, as at 28. The multi-layer liposuction is more specifically defined by accomplishing a superficial layer liposuction 30, a deep layer liposuction 32 and an intermediate layer liposuction 34. It should be noted that the order or sequence of applying the liposuction to the superficial, deep and/or intermediate layers may vary. A skilled surgeon therefore can accomplish liposuction at the different superficial, deep or intermediate layers in any preferred order or sequence and is not limited to the specific order of application.

Subsequently, postoperative management of the patient as at 36 is accomplished, as will be set forth in greater detail hereinafter.

In the development and perfection of the UAHDL surgical procedure of the present invention, a trial was performed utilizing 306 patients treated in two separate series. Satisfactory results were obtained in 257 patients or 84% of the patients involved in the trial. No cases of skin nacrosis occurred and minor complications included 20 cases of seroma or fluid build-up, nine cases of port site burns and five cases of prolonged swelling. The conclusions clearly indicated that the UAHDL or "ultrasound assisted high definition liposculpture" is an aggressive approach to body contouring that enables the surgeon to perform body sculpting of the superficial tissues to define the three-dimensional surface musculature in a wide range of patients.

Details of the surgical trial included a first step of preoperative marking performed when the patient is initially in a supine orientation and completed when the patient is an upright, standing position. During the preoperative marking, the physician should recognize that surface anatomy varies between men and women wherein the "V" shape is desirable in the male back as is a convexity over the inferior portion of the obliquus muscle. In women, the landmark may include the serratus interior, the rectus abdominis, the external oblique, the iliac crest and the inguinal ligaments.

In the infiltration procedure 14, as represented in the accompanying Figure, both superficial and deep infiltration were performed using a standard saline solution with the addition of epinephrine in indicated volumes as set forth above. Symmetric volumes were infiltrated about the surgical site and specifically on each side of the body torso. The infiltration aspiration ratio was 1.5-2:1. Detailed infiltration was performed in areas that required more superficial works such as the waist and perigluteal area in women, the indentation of the rectus and serratus muscles in men and the areas of skin laxity, such as the hypogastrium. In anticipation of the use of ultrasound technology, the exact amounts of infiltration in each area and the estimated time of ultrasound use were recorded. An estimated 10 minutes was allowed after infiltration before commencement of the ultrasound emulsification in order to allow time for effective vasoconstriction.

The emulsification procedure was performed in accordance with the chart of volume infiltrated in the same order as the infiltration. The duration of ultrasound treatment was 1 minute per each 100 mL of infiltration, but the clinical end point was the loss of resistance. Areas of high de-bulking, such as large fat deposits, were treated, utilizing ultrasound technology, with 3.7 mm or 2.9 mm, 3-groove probe, at 80% power in a continuous mode. The back and posterior arms were treated using a 3.7 mm, 1-groove probe in continuous mode. Thin skin or delicate areas such as the inner thighs, waist and neck were treated using a 2.9 mm, 3-groove probe at 60% power in a pulsed mode. Differential emulsification was performed for each muscle group and the muscle lines. Superficial emulsification was performed using a 2.9 mm, 3-groove probe, always in a pulsed mode. In some cases, additional infiltration was performed prior to the superficial emulsification. It was noted that the superficial emulsification addresses the immediate sub-dermal plane, thereby allowing enhanced skin retraction and compensating for areas of muscle or fascial laxity. The emulsification focused on three lamellar layers. The clinical end point in superficial layer emulsification was also the loss of resistance, but the skin was never allowed to become warmer than the hands of the surgeon. The achievement of loss of resistance in this layer without heat generation is a factor in avoiding complications.

In the associated de-bulking technique, ventilated cannulas with specialized small holes which prevent clogging achieved optimal efficiency and provided gentle suction that minimizes trauma. De-bulking began at the areas of fat deposits in the deep layer, using 3.7-mm or 4.6-mm cannulas and continued in the mid-lamellar layer and between muscle groups, avoiding aspiration against delicate sub-dermal layers.

Superficial emulsification and extraction steps were performed selectively over the muscular frame in each area to define relevant anatomy for each muscle group (i.e. linea alba and its tendinous insertions, the pectoral inferior line, inguinal ligament), using a 2.9-mm probe emulsification and 3.0-mm cannula aspiration. Superficial emulsification and extraction were performed in the sub dermal lamellar layer. From an artistic point of view this step is analogous to the initial two-dimensional sketch of any drawing.

The transitioning technique further comprises the blending of the framing and typography of the muscles. More specifically using a 3.7-mm or 4.6-mm cannula, some of the remaining fat deposits over each of the muscle grouping was de-bulked, while the surface overlying the creases over the mid-lamellar layer was smoothed, thus improving the definition of the superficial anatomy landmarks. Transitioning creates the natural but well defined appearance that was sought to be achieved. From an artistic point of view, the transitioning step is equivalent to the addition of "shadows and light" to create a three-dimensional "rendering". The surgical end point was the definition of the lateral borders of the muscles while retaining a thin layer of fat in the range of 1 cm in a pinch test.

In the postoperative management 36 open drains were left for 48-72 hours in the sacral area in female patients or in the inguinal area in male patients. Postoperative care included the use of a mild compression garment, deep vein thrombosis stockings and a cotton-lamented soft foam band, which may be used for a period of up to four weeks. Patients were given oral antibiotic and anti-inflammatory drugs for a short period of time. After 48 hours, patients were allowed to start postoperative lymphatic drainage massages and adjunctive external ultrasound of one hour sessions, once a day for ten days.

Patients were followed postoperatively at 1, 3, 6, 12 and 24 weeks. The anatomical definition accomplished at surgery was lost in the early initial postoperative period because of swelling. However, the accomplished definition started to reemerge at 3-4 weeks postoperative. Patients also experienced indurations during the first 6-8 weeks postoperatively that tended to be migratory, particularly in the areas of definition where contour was created by superficial and transitioning work. In all cases, these indurations disappeared completely by the third month. Patients also experienced cyclic swelling that varied the appearance of definition throughout the day. At approximately 4 months postoperatively, the swelling abated and patients could see about 95% of their final results and accomplished muscular definition.

Finally, it should be recognized that although the preferred embodiments of the present invention utilize an ultrasound technology, such as but not limited to a VASER technology, other techniques and instruments to emulsify and remove fat may also be utilized so long as they can provide the desired targeted area of effect.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A surgical procedure for performing liposculpture on the human body, said surgical procedure comprising:
   marking at least one portion of the body to define a surgical site,
   marking substantially 360° about the at least one portion of the body which defines the surgical site,
   forming a plurality of anatomical incisions over the substantially 360° of the surgical site,
   introducing a predetermined quantity of solution through the plurality of anatomical incisions about the surgical site,
   performing multi-layer emulsification of fat deposits at the surgical site, including a superficial layer emulsification, an intermediate layer emulsification and a deep layer emulsification of fat deposits, and
   extracting emulsified fat deposits from multiple layers at the surgical site, including at least a deep layer; a superficial layer and an intermediate layer.

2. A procedure as recited in claim 1 further comprising defining the at least one portion of the body which defines the surgical site as at least one limb of the body.

3. A procedure as recited in claim 1 comprising performing the multi-layer emulsification using ultrasound technology.

4. A procedure as recited in claim 1 wherein the predetermined quantity of solution is epinephrine with a saline solution.

5. A procedure as recited in claim 1 further comprising introducing the predetermined quantity of solution through the plurality of anatomical incisions using infiltration cannulas.

6. A procedure as recited in claim 1 comprising accomplishing a sub-dermal superficial release of fat deposits and thereby produce skin retraction by performing the superficial layer emulsification of fat deposits.

7. A procedure as recited in claim 6 comprising creating predetermined anatomical landmarks by using underlying anatomical structures as a guide for the superficial layer emulsification.

8. A procedure as recited in claim 1 comprising extracting the fat deposits which primarily create deformities about the surgical site by performing liposuction at the deep layer.

9. A procedure as recited in claim 8 comprising making the portion of the body correspond to predetermined anatomical landmarks of muscle tissue about the surgical site by performing liposuction at the superficial layer.

10. A procedure as recited in claim 9 comprising distinguishing differences between surgically affected anatomical sections of the surgical site by performing liposuction at the intermediate layer.

11. A procedure as recited in claim 1 further including transitioning superficial anatomy landmarks comprising extracting at least some remaining fat deposits existing over muscle groupings associated with the superficial anatomy landmarks and smoothing the surfaces over the associated superficial anatomy landmarks.

12. A procedure as recited in claim 1 further comprising defining the at least one portion of the body which defines the surgical site as a torso of the body.

\* \* \* \* \*